(12) United States Patent
Suominen

(10) Patent No.: US 7,646,848 B2
(45) Date of Patent: Jan. 12, 2010

(54) GONIOMETER

(75) Inventor: Lasse Suominen, Säynätsalo (FI)

(73) Assignee: Stresstech Oy, Vaajakoski (FI)

( * ) Notice: Subject to any disclaimer, the term of this patent is extended or adjusted under 35 U.S.C. 154(b) by 163 days.

(21) Appl. No.: 11/791,341

(22) PCT Filed: Nov. 24, 2005

(86) PCT No.: PCT/FI2005/000505

§ 371 (c)(1),
(2), (4) Date: May 23, 2007

(87) PCT Pub. No.: WO2006/056647

PCT Pub. Date: Jun. 1, 2006

(65) Prior Publication Data

US 2007/0291899 A1    Dec. 20, 2007

(30) Foreign Application Priority Data

Nov. 29, 2004    (FI) .................................. 20041538

(51) Int. Cl.
*G01N 23/20* (2006.01)
(52) U.S. Cl. ......................................................... 378/81
(58) Field of Classification Search .................. 378/70, 378/73, 79, 81, 83, 193, 196, 197
See application file for complete search history.

(56) References Cited

U.S. PATENT DOCUMENTS

| 3,728,541 | A | * | 4/1973 | Rabinovich et al. ............ 378/77 |
| 4,058,731 | A | | 11/1977 | Müller et al. |
| 4,561,062 | A | | 12/1985 | Mitchell |
| 5,073,912 | A | | 12/1991 | Kobayashi et al. |
| 6,064,717 | A | | 5/2000 | Ortega et al. |
| 6,721,393 | B1 | | 4/2004 | Brauss |
| 6,853,706 | B2 | | 2/2005 | Brauss et al. |
| 6,893,212 | B2 | | 5/2005 | Galassi et al. |
| 6,925,146 | B2 | | 8/2005 | Brauss et al. |
| 2003/0012334 | A1 | * | 1/2003 | Kurtz et al. ................... 378/73 |
| 2003/0161722 | A1 | | 8/2003 | Galassi |
| 2004/0165697 | A1 | | 8/2004 | Brauss |
| 2004/0184580 | A1 | | 9/2004 | Brauss |
| 2005/0141667 | A1 | | 6/2005 | Berti |
| 2005/0195942 | A1 | | 9/2005 | Brauss |
| 2005/0281375 | A1 | | 12/2005 | Brauss |

FOREIGN PATENT DOCUMENTS

| DE | 101 39 645 A1 | 3/2003 |
| EP | 0 512 620 A2 | 5/1992 |
| JP | 58-38845 A | 3/1983 |
| WO | WO-03/060498 A1 | 7/2003 |

* cited by examiner

*Primary Examiner*—Irakli Kiknadze
(74) *Attorney, Agent, or Firm*—Birch, Stewart, Kolasch & Birch, LLP

(57) ABSTRACT

The invention relates to a goniometer (1) and a method for measuring stresses and characterizing microstructure of particles. The goniometer comprises frame (4), a measurement head (7, 8, 9, 10) movably adapted to the frame (4) by a first linear movement unit (5), second linear movement unit (6) and a tilting movement unit (16), for performing measurement at a measurement point. According to the invention the axis of rotation (12) of the tilting movement unit (16) does not coincide with the measurement point, and the device has means (17) for creating arc-formed movement of the measurement head (7, 8, 9, 10) during the measurement with said movement units (5, 6, 16).

18 Claims, 5 Drawing Sheets

GONIOMETER

The present invention relates to a goniometer.

The invention also relates to a method for moving the measurement head of a goniometer.

BACKGROUND OF THE INVENTION

Description of Background Art

The invention is a portable goniometer or sometimes called diffractometer for measuring stresses and characterizing microstructure. The main purpose of the portability is to be able to measure large components or structures as crankshafts, pipelines, bridges etc.

Because of the economical and environmental reasons, the general trend is towards lighter components and structures in manufacturing. Environmental issues are especially important when all kinds of vehicles are in question. Less weight means less fuel consumption and thus less pollution. To achieve lighter structures increased material strengths and/or lower margin of safety needs to be accepted. The high strength materials mean higher demand of the material handling as deforming, welding, machining etc. Due to all these factors quality control is strongly increasing. A new property, which has been taken into account more and more often recently, is evaluation of residual stresses compared to traditional crack detection. Residual stresses increase or decrease straightforwardly the endurance of the components or the structures, when they are combined with load stresses.

The most common stress measurement method is based on X-ray diffraction, by which the lattice plane distances (d), distances between atoms are measured. The compressive stress decreases the lattice distance and correspondingly tensile stress increases it. Specific lattice planes are measured to many directions compared to the surface normal of the measurement point. Due to the stresses on the sample surface the lattice distance changes as the function of the tilt angle. In order to be able to measure lattice planes in different tilt angles, the incident and diffracted beams angle compared to the normal of the measurement surface has to be changed with known amounts. In the laboratory diffractometers this has been done by tilting the sample. In the portable diffractometers respectively the goniometer including a measurement head comprising of X-ray tube and detector(s) is tilted. In the case of position sensitive detector, the detector is fixed together with the X-ray tube, and in the case of a single channel detector system, the detector is moving compared to the X-ray tube.

The two most important factors on residual stress measurement by X-ray diffraction are that the distance between the measurement point and the detector stays constant and that the incident beam hits accurately the measurement point in every tilt position. Traditionally this has been done typically by a cradle (arc), which is located under the measurement head. This technology is described e.g. in U.S. Pat. No. 5,125, 016. This kind of design has many disadvantages:

1) the structure of the cradle (arc) is complicated,
2) the measurement distance is fixed,
3) cradle (arc) under of the measurement head can stumble on the sample,
4) if the measurement head is under the cradle, the size of the arc becomes large and bulky, and thus less portable.

From U.S. Pat. No. 6,064,717 is known a measurement device with a X-ray tube and detector attached to two different pivoted robot arms. The complicated pivoted arm structures are very difficult to construct accurate enough for X-ray diffraction measurements due to unavoidable backlashes in multiple pivot points. Even if these problems could be minimized to an acceptable level, the costs would be very high. This solution is not portable.

In US 2004/0165697 and US 2004/0184580 are described solutions, where a mechanical cradle is used for the rotational movement, but some basic adjustments are made by linear motors. The same disadvantages as other mechanical cradles apply also this solution. Especially in US 2004/0184580 the measurement point has to be on the rotational axis of the tilting movement unit and this limits the adjustment of the device for different measurement objects.

SUMMARY AND OBJECTS OF THE INVENTION

The present invention is based on implementing the movement of the measurement head during the measurement by two linear movements combined with a rotational movement of the actual measurement head.

In one preferred embodiment of the invention the axis of rotation of the tilting movement unit is movable during the measurement and does not coincide with the measurement point.

In one preferred embodiment of the invention the linear movements are essentially a) horizontal movement and b) vertical movement.

The three most important advantages of this new invention are:

1) there is no cradle (arc) or other structures but detectors under the measurement head. This means less stumbling with complicated samples.
2) The measuring distance is freely selectable by the software.
3) Simple design, for which most of the components can be bought. The complicated, inaccurate and costly structure of U.S. Pat. No. 6,064,717 can be avoided Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

In the following, the invention is examined on the basis of an example of an embodiment according to the accompanying drawings.

DETAILED DESCRIPTION OF THE PREFERRED EMBODIMENTS

Figure 1:
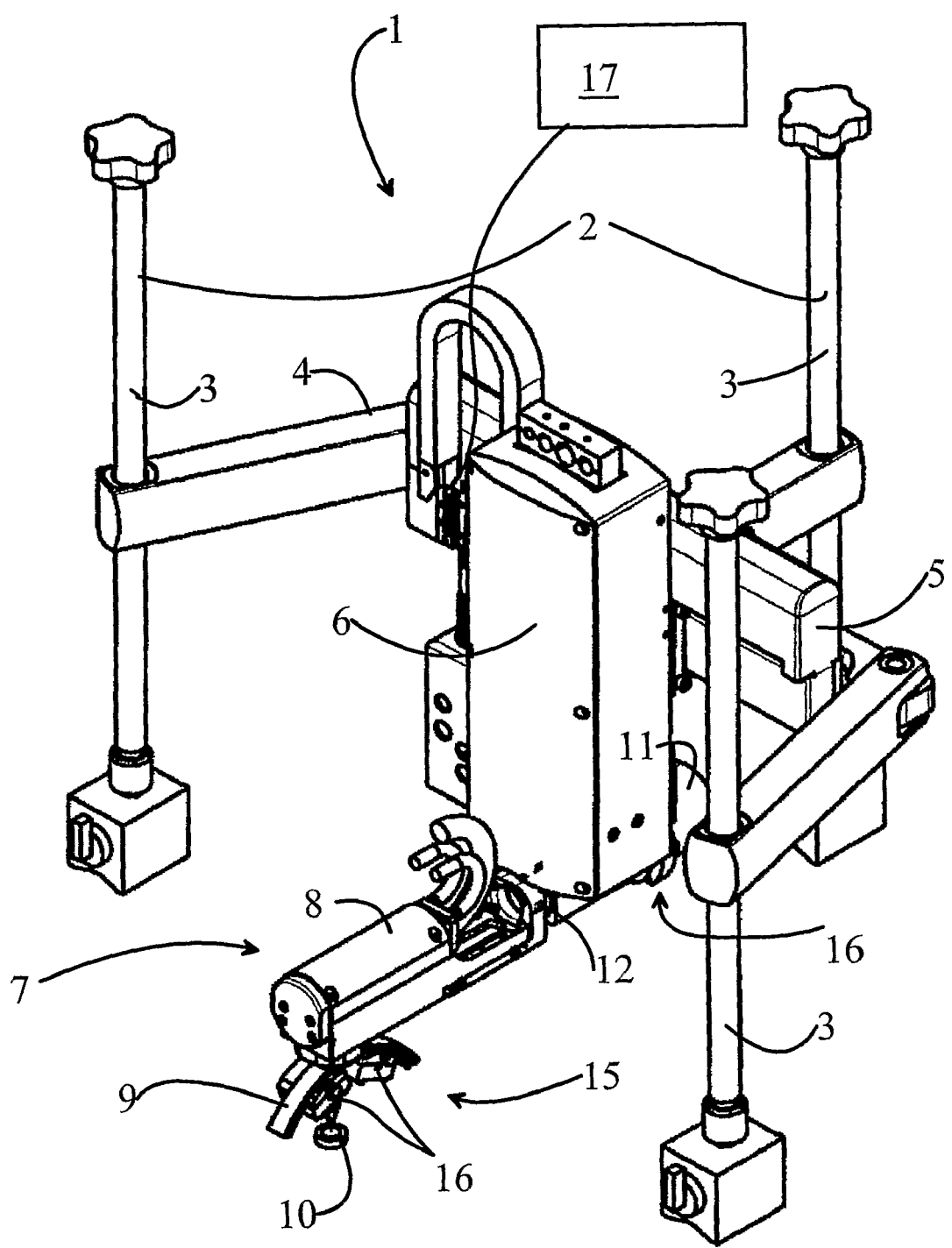
FIG. 1 shows as a perspective view one goniometer in accordance with the invention.

In the following detailed description of the invention the following terms are used:
1 goniometer
2 tripod stand
3 adjustable support
4 support frame
5 horizontal movement unit
6 vertical movement unit
7 measurement head
8 X-ray tube housing
9 detector arc
10 collimator
11 angle sensor
12 tilting axle
13 tilting motor
14 screw gear
15 collimator assembly
16 tilting movement unit
17 control unit
18 detector
30 path of the measurement head 7
31 measurement point According to FIG. 1 the goniometer 1 for measuring stresses includes a frame 4 with three adjustable supports 3 forming a tripod stand. Further the device includes a measurement head 7 which is movably attached to the frame 4 by a first linear movement unit 5, second linear movement unit 6 and a tilting movement unit 16, for performing measurement at a measurement point situated beneath the measurement head at desired distance. Due to the fact that the arc-shaped movement of the measurement head 7 is during the measurement created by the movement units 5, 6 and 16, the axis of rotation 12 of the tilting movement unit 16 does not coincide with the measurement point like in the cradle solutions. For the arc-shaped movement of the measurement head 7 the device has means control means for creating arc-formed movement with said movement units 5, 6, 16.

So, the four main components of the centerless goniometer are two units for linear movement; one for vertical 6 and another one for horizontal 5 movement. The third component is the measurement head 7, which is attached to the lower end of the unit for vertical movement 6. The measurement head 7 can be tilted around its longitudinal axis, tilting axle 12 by a tilting movement unit 16. The measurement head 7 includes the X-ray tube housing 8 as well as detectors 18 attached to the detector arc 9. Especially the tilting angle of the measurement head 7 has to be accurate, meaning accuracy better than 0.01 degree. The angle is measured by the angle sensor 11 positioned at the end of the tilting axle 12.

Figure 2:
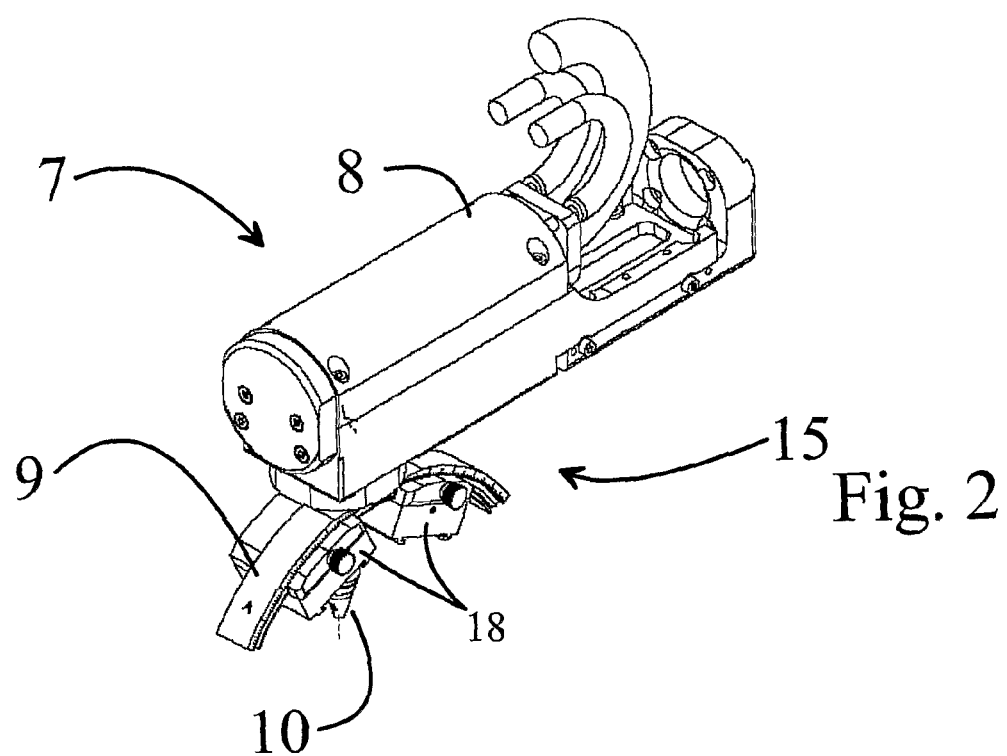
FIG. 2 shows as a perspective view a X-ray tube housing in accordance with the invention.

According to FIG. 2 inside the measurement head 7 detector arc, 9, collimator 10 and detectors 18 form a collimator unit 15.

The invention works so that the measurement head 7 follows precisely the predetermined circular path around the measurement point. The circular path is formed by the linear vertical 6 and horizontal 5 movement units together with the tilting movement unit 16. The X-ray beam, which is directed to the measurement point through the collimator 10, hits the correct position always exactly even when moving up and down or horizontally and when tilted. In addition, to the accurate tilting of the measurement head 7, the distance between the measurement point and the detectors has to be measured in an accuracy better than 0.05 mm. The movements by all three motors have to be synchronized so that the measurement head 7 moves in the circular path all the time. The synchronization and control are performed either by an internal control unit (not shown) or with an external control unit 17, which can be a normal tabletop computer equipped with a suitable control program for controlling the motors of each movement unit 5, 6 and 16. Of course, also a combination of internal and external control units may be used for control purposes.

Essential to the invention is that the radius of the goniometer can be freely changed with the software in the range of the length of the linear movement units 5 and 6.

The centerless goniometer according to the invention may also include in one preferred embodiment a laser pointer, spring loaded collimator 10 for distance measurement and optional laser distance measurement system. In practice, the spring loaded collimator is used for distance measurement simply by lowering the measurement head so far to the measurement point that the collimator touches the measurement point and this touching is recorded, and the corresponding distance between the measurement position and "touching" is determined e.g. by position sensors or from he control data. The measurement is advantageously done at the beginning of each measurement. Distance measurements systems are used to find the position of the measurement point as relation to the measurement head 7. Laser beam is guided through the collimator 10 by mirrors. The goniometer may also include a standard shutter structure and safety features.

Figure 4:
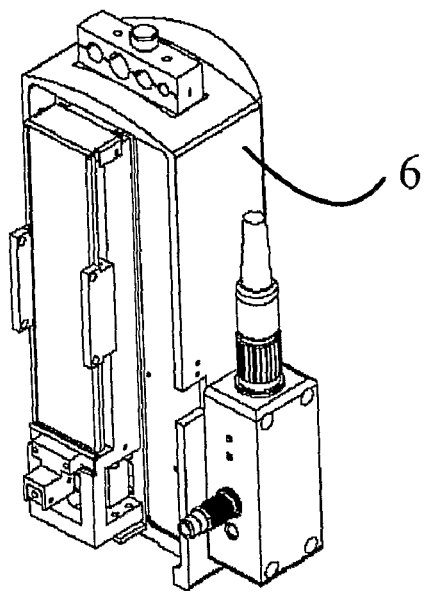
FIG. 4 shows as a perspective view a vertical movement unit in accordance with the invention.
Figure 5:
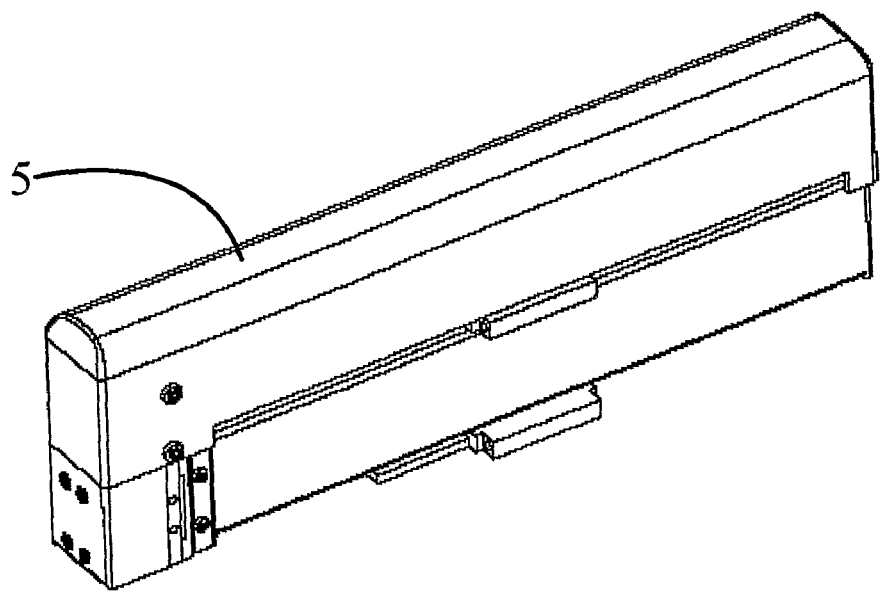
FIG. 5 shows as a perspective view a horizontal movement unit in accordance with the invention.

FIGS. 4 and 5 show vertical and linear movement units more closely.

Figure 3:
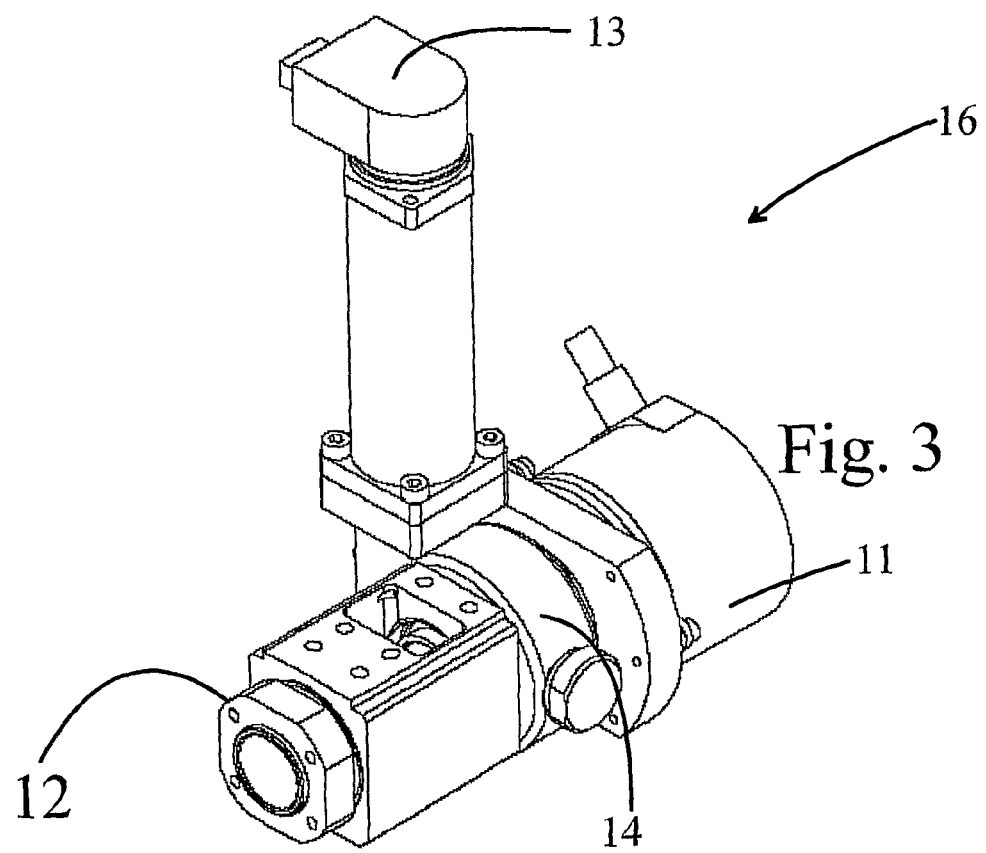
FIG. 3 shows as a perspective view a tilting movement unit in accordance with the invention.

In the following some important features for implementation of the invention:

Mechanics:
1) According to FIG. 3 tilt angle control demands absolute angular position sensor 11, which directly coupled to tilt shaft 12. Tilt movement is controlled with an encoder because angular position sensor's pulse amount is too small. The gear 14 has to be with as small backlash as possible.
2) The system may include a programmable chip which can automatically detect the X-ray tube, e.g. by its serial number. This makes it possible to keep track automatically operating time and also tube type, which affects to tube control parameters; improves quality and human errors. Same chip may also include the temperature control of the tube.
3) System may include also a photomicrosensor (not presented) to control accurately the measurement distance. Accuracy of this has to be better than 0.01 mm. The sensor may be positioned e.g. on the bottom of the X-ray tube housing 8.
4) The system may include a laser diode and mirror in shutter to point out measurement point. The shutter is positioned inside of the X-ray tube housing 8. The laser light is conducted through the collimator 10 by a mirror in the shutter. Laser beam comes out from the collimator 10 when shutter is closed. The shutter is round bar with hole. Shutter is open and closed by gearmotor.

5) Collimator sliding tube is preferably diamond coated to decrease friction and improve through that the accuracy of the measurement distance.
6) The system may include a joystick for manual movements.

Control Electronics:
1) In one preferred embodiment of the invention there are two electronic boards in the goniometer: (a) motor control board and (b) microprocessor board with all needed auxiliary functions.
2) Motor control board is built based on programmable FBGA components which make it possible to change flexibly for example the types of motors.
3) Microprocessor board controls the position of the system and gives needed command to motor control board. The board is connected to other system components 17 through Ethernet link. Board also includes detector connections and other auxiliary connections.

Mechanical design makes it possible to correct many alignment errors with software functions as beam center position and possible mechanical inaccuracies.

Figure 6A:
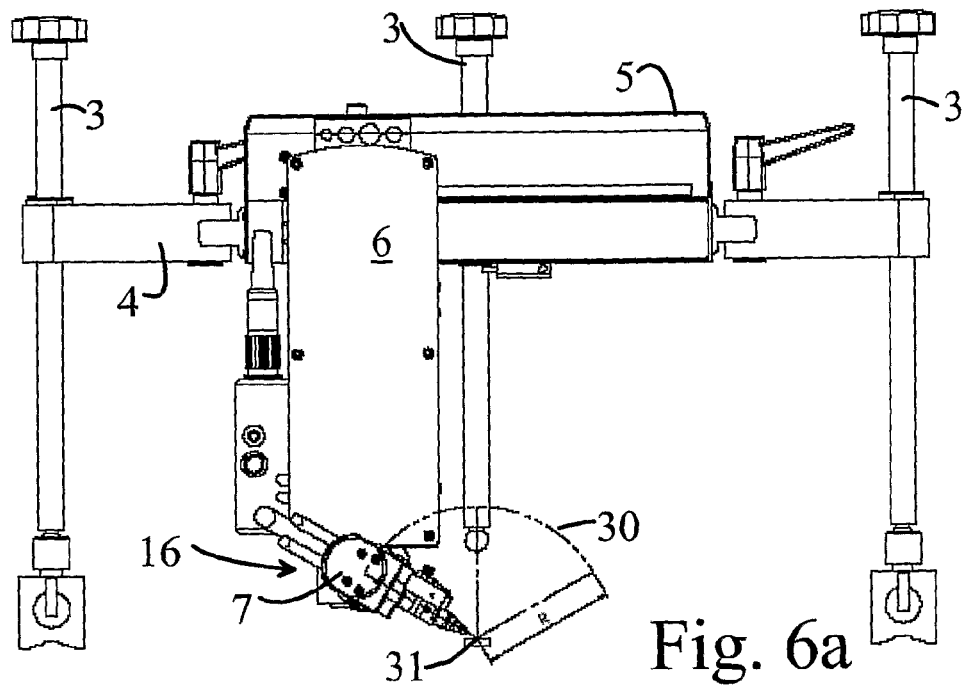
FIGS. 6a-6c show as a front views the function of the goniometer of FIG. 1.
Figure 6B:
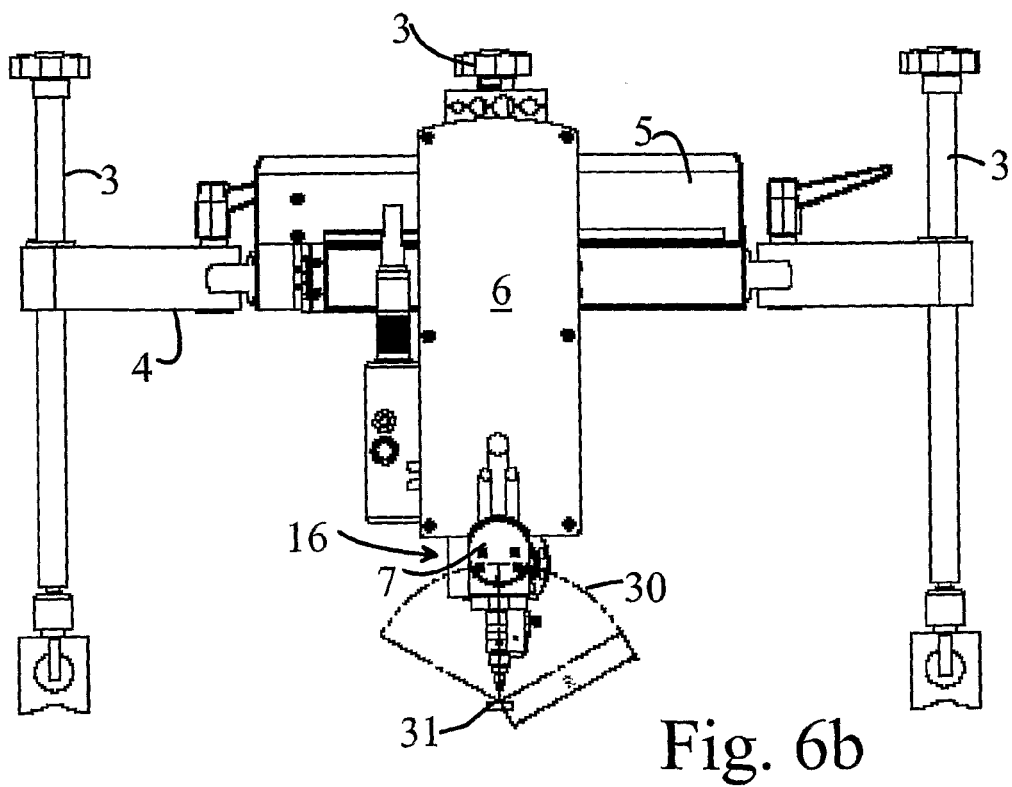
Figure 6C:
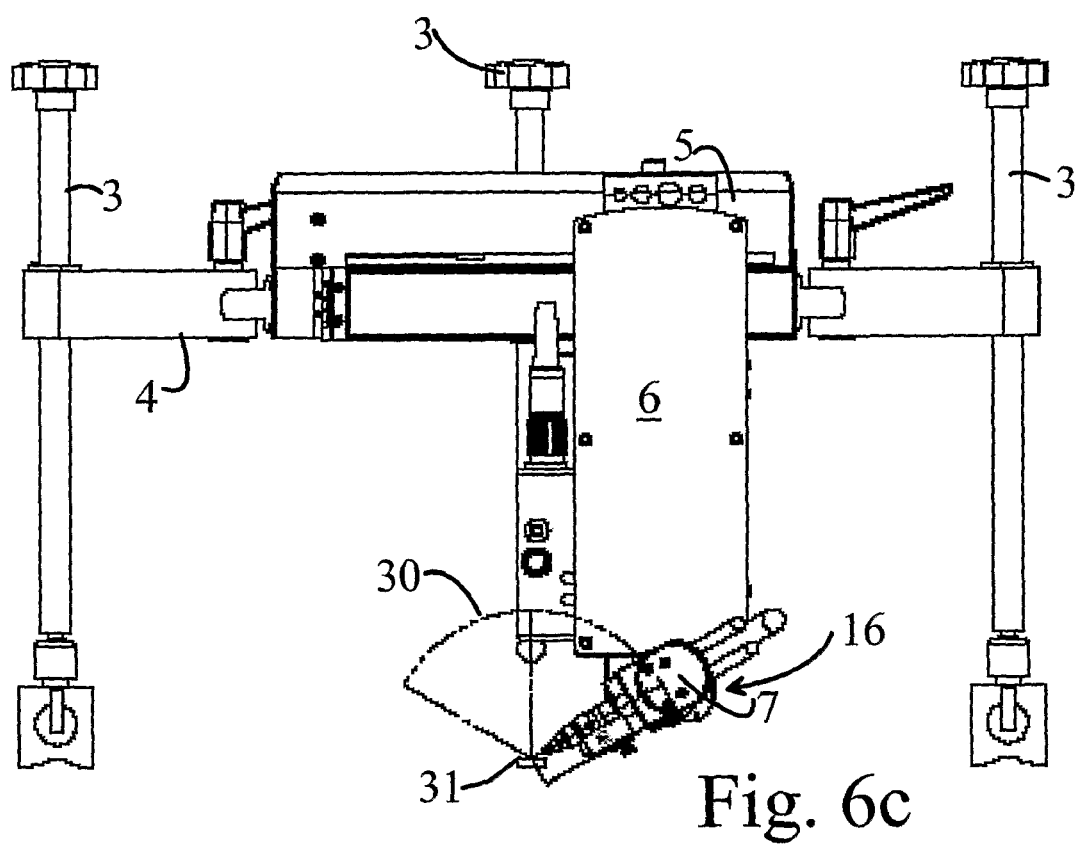

The function of the goniometer is described in more detail in connection with FIGS. 6a-6c. The arc 30 shows the path of the measurement head 7 during the measurement. The measurement head during the measurement always directed to the measurement point 31. FIG. 6a shows the measurement head 7 in the leftmost position, FIG. 6b in the center position and FIG. 6c on the rightmost position. One complete measurement requires at least these three positions. The tilting of the measurement head is performed by the tilting movement unit 16 and the arc movement by horizontal movement unit 5 together with vertical movement unit 6.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

The invention claimed is:
1. A goniometer (1) for measuring stresses and characterizing microstructure of particles, comprising:
a frame (4),
a measurement head (7, 8, 9, 10) movably adapted to the frame (4) by a first linear movement unit (5), second linear movement unit (6) and a tilting movement unit (16), for performing measurement at a measurement point (31),
wherein the axis of rotation (12) of the tilting movement unit (16) does not coincide with the measurement point (31), and
the device has means (17) for creating arc-formed (30) movement of the measurement head (7, 8, 9, 10) during the measurement with said movement units (5, 6, 16) without the use of a cradle under the measurement head.

2. An apparatus according to claim 1, characterized in that it comprises an encoder for measuring the tilting angle.
3. An apparatus according to claim 1, characterized in that gear (14) of the tilting movement unit (16) has a reduced backlash.
4. An apparatus according to claim 1, characterized in that it comprises means for automatically detecting the X-ray tube.
5. An apparatus according to claim 1, characterized in that it comprises temperature control means for the X-ray tube.
6. An apparatus according to claim 1, characterized in that it comprises a photomicrosensor for controlling accurately the measurement distance with accuracy be better than 0.01 mm.
7. An apparatus according to claim 1, characterized in that it comprises a laser diode and mirror in shutter to point out measurement point.
8. An apparatus according to claim 1, characterized in that the collimator sliding tube is diamond coated to decrease friction and improve through that the accuracy of the measurement distance.
9. An apparatus according to claim 1, characterized in that it comprises a joystick for manual movements.
10. A method for controlling a goniometer (1) used for measuring stresses and characterizing microstructure of particles, comprising the following steps:
moving a measurement head (7, 8, 9, 10) along a circular path (30) around a measurement point (31),
carrying out the movement (30) by a combination of two first linear movements (5, 6) combined with one tilting movement (16) without the use of a cradle under the measurement head.
11. An apparatus according to claim 10, characterized in that the tilting movement is carried out such that the axis of rotation (12) of the tilting movement unit (16) does not coincide with the measurement point (31).
12. A method according to claim 10, characterized in that an encoder is used for measuring the tilting angle.
13. A method according to claim 10, characterized in that the X-ray tube is automatically detected.
14. A method according to claim 10, characterized in that the temperature control is performed for the X-ray tube.
15. A method according to claim 10, characterized in that a photomicrosensor is used for controlling accurately the measurement distance with accuracy be better than 0.01 mm.
16. A method according to claim 10, characterized in that a laser diode and mirror is used in shutter to point out measurement point.
17. A method according to claim 10, characterized in that the collimator sliding tube is diamond coated to decrease friction and improve through that the accuracy of the measurement distance.
18. A method according to claim 10, characterized in that a joystick is used for manual movements.

* * * * *